(12) United States Patent
Carter et al.

(10) Patent No.: US 9,171,482 B2
(45) Date of Patent: Oct. 27, 2015

(54) PROVIDING DIET AND EXERCISE PLANS WITH REAL TIME TRACKING, MODIFICATION, AND NOTIFICATION

(71) Applicants: Abraham Carter, Salt Lake City, UT (US); David Scott, North Salt Lake City, UT (US)

(72) Inventors: Abraham Carter, Salt Lake City, UT (US); David Scott, North Salt Lake City, UT (US)

(*) Notice: Subject to any disclaimer, the term of this patent is extended or adjusted under 35 U.S.C. 154(b) by 238 days.

(21) Appl. No.: 13/763,472

(22) Filed: Feb. 8, 2013

(65) Prior Publication Data

US 2013/0209972 A1    Aug. 15, 2013

Related U.S. Application Data

(60) Provisional application No. 61/597,077, filed on Feb. 9, 2012.

(51) Int. Cl.
*G09B 19/00* (2006.01)
*G06F 19/00* (2011.01)

(52) U.S. Cl.
CPC ........ *G09B 19/0092* (2013.01); *G06F 19/3475* (2013.01); *G06F 19/3481* (2013.01)

(58) Field of Classification Search
CPC . G09B 19/00; G09B 19/0038; G09B 19/0092
USPC .................................................. 434/127, 247
See application file for complete search history.

(56) References Cited

U.S. PATENT DOCUMENTS

| | | | | |
|---|---|---|---|---|
| 5,890,128 | A * | 3/1999 | Diaz et al. ........................ | 705/2 |
| 7,534,206 | B1 * | 5/2009 | Lovitt et al. .................... | 600/300 |
| 2005/0240444 | A1 * | 10/2005 | Wooten et al. .................... | 705/3 |
| 2006/0199155 | A1 * | 9/2006 | Mosher ........................ | 434/127 |
| 2011/0087137 | A1 * | 4/2011 | Hanoun ........................ | 600/587 |
| 2011/0281249 | A1 * | 11/2011 | Gammell et al. ............. | 434/247 |

* cited by examiner

*Primary Examiner* — Kesha Frisby
(74) *Attorney, Agent, or Firm* — Michael F. Krieger; Kirton McConkie

(57) ABSTRACT

The present invention extends to methods, systems, and computer program products for providing diet and exercise plans and for providing real time tracking and notifications of the user's conformance with a plan. The plan can be dynamically updated in real time based on the user's compliance with the plan. In some embodiments, the present invention can be implemented using a user's mobile phone that communicates with one or more other computing devices that are incorporated into exercise devices.

19 Claims, 2 Drawing Sheets

200

201
receive, by a computing device, a diet and exercise plan of a user, the diet and exercise plan including a target number of calories to burn during a time period, the target number of calories being based on the number of calories consumed by the user in the time period and a total number of calories burned by the user during the time period 202
generate and display, to the user, a first recommended workout to perform using a first of a plurality of exercise devices 203
receive, from the first exercise device and in response to the user using the first exercise device, a number of calories burned by the user while using the first exercise device 204
deduct the number of calories burned by the user while using the first exercise device from the target number of calories 205
based on the target number of calories that remain after the deduction of the number of calories burned by the user while using the first exercise device, generate and display to the user, a second recommended workout to perform using a second of the plurality of exercise devices

FIG. 2

PROVIDING DIET AND EXERCISE PLANS WITH REAL TIME TRACKING, MODIFICATION, AND NOTIFICATION

CROSS-REFERENCE TO RELATED APPLICATIONS

This application claims the benefit of U.S. Provisional Patent Application No. 61/597,077, filed Feb. 9, 2012, titled "Method and System for Providing Diet and Exercise Plans and Providing Real Time Tracking and Notification."

BACKGROUND

Diet and exercise plans have been common for several generations. Individuals wishing to lose weight typically adhere to a preplanned diet and then periodically weigh themselves to verify efficiency. Such plans are often inefficient because they do not provide useful information in a time effective manner.

For example, most people view weight loss as the ultimate goal, but scales provide no feedback regarding whether the individual's current actions are effective. In other words, the user's individual choices during the day regarding what to eat and how to exercise determine whether the individual will lose weight. However, a scale only provides useful feedback after these individual choices have been made and the result of the choices has been manifest.

Many devices exist to assist the individual in tracking caloric intake and in tracking calories burned during an exercise. However, these devices often provide incomplete information and are difficult to use. For example, many web-based diet and exercise trackers exist, but require the individual to manually input information regarding what was eaten and what exercises were performed during a day.

BRIEF SUMMARY

The present invention extends to methods, systems, and computer program products for providing diet and exercise plans and for providing real time tracking and notifications of the user's conformance with a plan. The plan can be dynamically updated in real time based on the user's compliance with the plan. In some embodiments, the present invention can be implemented using a user's mobile phone that communicates with one or more other computing devices that are incorporated into exercise devices.

In one embodiment, the present invention is implemented as a method for providing a dynamically updated diet and exercise plan. A diet and exercise plan of a user is received by a computing device. The diet and exercise plan includes a target number of calories to burn during a time period. The target number of calories is based on the number of calories consumed by the user in the time period and a total number of calories burned by the user during the time period. A first recommended to perform using a first of a plurality of exercise devices is generated and displayed to the user.

In response to the user using the first exercise device, a number of calories burned by the user while using the first exercise device is received from the first exercise device. The number of calories burned by the user while using the first exercise device is deducted from the target number of calories. Then, based on the target number of calories that remain after the deduction of the number of calories burned by the user while using the first exercise device, a second recommended workout to perform using a second of the plurality of exercise devices is generated and displayed to the user.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 2 illustrates a flowchart of an exemplary method for providing a dynamically updated diet and exercise plan.

DETAILED DESCRIPTION

Figure 1:
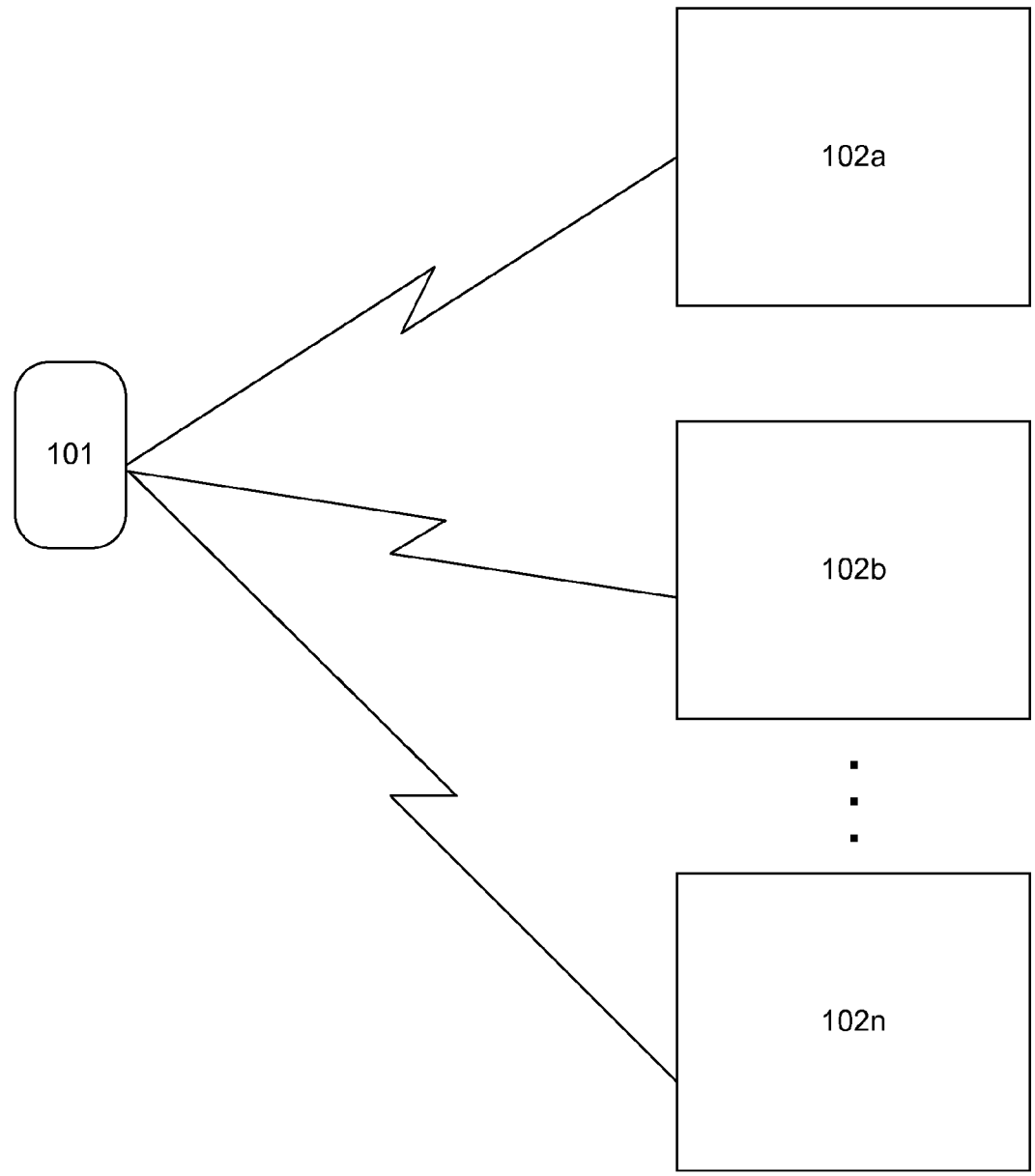
FIG. 1 illustrates an exemplary computing environment in which the present invention can be implemented.

The present invention extends to methods, systems, and computer program products for providing diet and exercise plans and for providing real time tracking and notifications of the user's conformance with a plan. The plan can be dynamically updated in real time based on the user's compliance with the plan. In some embodiments, the present invention can be implemented using a user's mobile phone that communicates with one or more other computing devices that are incorporated into exercise devices.

In one embodiment, the present invention is implemented as a method for providing a dynamically updated diet and exercise plan. A diet and exercise plan of a user is received by a computing device. The diet and exercise plan includes a target number of calories to burn during a time period. The target number of calories is based on the number of calories consumed by the user in the time period and a total number of calories burned by the user during the time period. A first recommended to perform using a first of a plurality of exercise devices is generated and displayed to the user.

In response to the user using the first exercise device, a number of calories burned by the user while using the first exercise device is received from the first exercise device. The number of calories burned by the user while using the first exercise device is deducted from the target number of calories. Then, based on the target number of calories that remain after the deduction of the number of calories burned by the user while using the first exercise device, a second recommended workout to perform using a second of the plurality of exercise devices is generated and displayed to the user.

Embodiments of the present invention may comprise or utilize special purpose or general-purpose computers including computer hardware, such as, for example, one or more processors and system memory, as discussed in greater detail below. Embodiments within the scope of the present invention also include physical and other computer-readable media for carrying or storing computer-executable instructions and/ or data structures. Such computer-readable media can be any available media that can be accessed by a general purpose or special purpose computer system.

Computer-readable media is categorized into two disjoint categories: computer storage media and transmission media. Computer storage media (devices) include RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other similarly storage medium which can be used to store desired program code means in the form of computer-executable instructions or data structures and which can be accessed by a general purpose or special purpose computer. Transmission media include signals and carrier waves.

Computer-executable instructions comprise, for example, instructions and data which, when executed by a processor, cause a general purpose computer, special purpose computer, or special purpose processing device to perform a certain function or group of functions. The computer executable instructions may be, for example, binaries, intermediate format instructions such as assembly language or P-Code, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like.

The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices. An example of a distributed system environment is a cloud of networked servers or server resources. Accordingly, the present invention can be hosted in a cloud environment.

FIG. 1 illustrates an exemplary computer environment 100 in which the present invention can be implemented. Computer environment 100 includes a portable computing device 101 and equipment computing devices 102a-102n. In a typical implementation, portable computing device 101 can comprise a user's mobile phone. However, portable computing device 101 can comprise other types of devices whether general purpose or specifically designed to implement the present invention.

Portable computing device 101 can be configured to receive input regarding a user's caloric intake. This input can be entered manually by the user, or can be estimated using photographs of what the user is about to eat. For example, the user can take a picture using a camera of a mobile phone acting as portable computing device 101. An app on the phone can include a database of foods that it can use to identify the type of food in the picture as well as a relative size or number of servings. Examples of how the food can be identified include using bar codes on packaging, using photo-recognition techniques which identify features on packaging or features of the food itself, etc. Regardless of how caloric intake is obtained, portable computing device 101 can track what the user has consumed in any given time period.

Equipment computing devices 102a-102n comprise the required components for a piece of exercise equipment to communicate with portable computing device 101. For example, equipment computing device 102a can be the on-board computing components of a treadmill that monitor a user's use of the treadmill and communicate this use to portable computing device 101. Such components can also receive communications from portable computing device 101 for displaying information on the treadmill, controlling one or more features of the treadmill, etc.

A treadmill is only one example of an equipment computing device. Equipment computing devices 102a-102n can be components of virtually any type of exercise equipment or other health related device such as a bike, an elliptical, a pedometer, a GPS watch, a scale, free weights, etc.

Portable computing device 101 and equipment computing devices 102a-102n can be configured to communicate using any type of wireless identification and communication including RFID, Bluetooth, or other technologies that allow wireless communications between devices. In one example, portable computing device 101 and/or equipment computing devices 102a-102n can be configured to identify when a user carrying portable computing device 101 is near a piece of equipment having an equipment computing device. The proximity of a user can cause the transmission of information regarding the user's diet and exercise plan between devices.

FIG. 1 represents an implementation where portable computing device 101 communicates directly with equipment computing devices 102a-102n. However, the present invention can equally be implemented using one or more intermediary computing devices such as a server. For example, any of portable computing device 101 and equipment computing devices 102a-102n can be configured to intercommunicate only directly, only via a server, or both directly and via a server.

Some or all of equipment computing devices 102a-102n can include the capability of displaying a user's diet and exercise plan on the associated piece of equipment, or of being configured in accordance with the user's diet and exercise plan. For example, when a user gets on a treadmill, the user's portable computing device 101 can transfer information about the user's plan which is displayed on the treadmill's display. Further, in some embodiments, the treadmill can suggest workouts or automatically commence workouts that will follow the user's plan. As or after the user uses the treadmill, the performance information tracked by the treadmill can be relayed back to portable computing device 101 to allow portable computing device 101 to update information regarding the user's performance and/or compliance with the plan.

Many different types of exercise and diet plan information can be displayed on a piece of equipment or on portable computing device 101. In the following description, the example of calories being displayed is primarily used to describe this feature. However, any other type of information can also be displayed, tracked, or updated using the techniques of the present invention. For example, a display of the types of exercises required or recommended to comply with the plan can be displayed or modified even in real time as the user performs exercises. Similarly, the display and update of calories can be in the form of calories burned during the time period, calories remaining to be burned during the time period, calories burned or remaining to be burned while performing a particular exercise, etc.

In another example, an equipment computing device may only be configured to route performance information back to portable computing device 101. For example, a pedometer may only be configured to relay information regarding the user's use of the pedometer, but may not be able to display information of the user's plan. Similarly, an equipment computing device can be configured to receive information from portable computing device 101 (e.g. control information for controlling the piece of equipment to perform a specific workout), and to report the user's performance while on the piece of equipment.

Portable computing device 101 can also be configured to allow manual input from the user for reporting exercise performance that is not tracked by an equipment computing device. For example, a user may run with a GPS watch that is not configured to communicate with portable computing device 101 or without any distance tracking device at all, but can still enter distance and time information manually for the run.

In some embodiments, equipment computing devices 102*a*-102*n* can include a scale. In such cases, as the user approaches the scale while carrying portable computing device 101, the scale can recognize the user (i.e. the user's device) and greet the user. The scale can also be configured to display to the user the planned exercise regimen for the day (by receiving the user's plan from device 101 and any relevant performance data already generated for the user). In some embodiments, a scale can be configured to communicate with other equipment computing devices 102*a*-102*n* (e.g. to relay plan information to the devices, to receive performance information, etc.).

One benefit of the ability to recognize a user of device 101 and to communicate plan information between devices 101 and 102*a*-102*n* is the ability to customize the user's plan in real time. For example, a user may start with a predetermined exercise regimen including a certain number of reps on multiple pieces of equipment. However, if during performance of the exercise regimen, it is determined that the user has performed differently (e.g. by spending more time on a particular piece of equipment, by consuming a different amount of calories than recommended in the plan, by performing different activities, etc.), the user's plan can be dynamically updated (e.g. reducing the recommended time to spend on one piece of equipment if the user spent more time than recommended on another piece of equipment, recommending a different piece of equipment for a next exercise if the user exercised on a different piece of equipment than recommended, etc.).

Since the exercise regimen can be constantly changing, one or more of equipment computing devices 102*a*-102*n* (as well as portable computing device 101) can display the updated exercise regimen when the user approaches to use the associated equipment. In the case that the user chooses to free style rather than follow a predetermined exercise program, the exercise computing device can simply display how many calories are left to be burned for that workout or that day (or display total calories burned, recommended number of calories to burn on the particular piece of equipment, or any other measure of the user's compliance with the plan). After the user has completed using the associated piece of equipment, the calories burned by the user while using the equipment can be routed to portable computing device 101 to allow the dynamic updating of the user's plan (e.g. subtracting calories burned from target calories remaining to be burned, adding calories burned to a total calories burned, modifying a remaining portion of the plan whether exercise related or diet related, etc.).

As stated above, based on the input of calories consumed (e.g. via manual input or automatic calculation based on pictures, scanned bar code, etc.) and calories burned (e.g. from equipment computing device 102*a*-102*n*), portable computing device 101 (or another connected computing device) can modify the user's diet and exercise plan in real time. For example, based on what the user has eaten and done during the day, the user's plan can be dynamically modified to reflect recommended activities to perform or recommended foods to consume to meet the plan's requirements for that day.

Additionally, the tracked exercise performance information can be uploaded to a server for use in a social media environment. This use can include displaying to friends the status of the user's compliance with the plan, challenging friends to perform an exercise regimen that the user has just performed, comparing the user's performance to another's user performance under the same or similar plan. In a particular example, the present invention can provide a social media environment where users can view a celebrity's exercise and diet plan as well as the celebrity's compliance with the plan. In this way, the users can compare their performance against that of the celebrity which may provide additional motivation in many cases.

In some embodiments, another user's plan or performance of a plan can be downloaded to portable computing device 101 or to one of equipment computing devices 102*a*-102*n* to allow the user to compare his current performance against the other user's plan or performance. For example, a user can download another user's treadmill workout to an equipment computing device on a treadmill to allow the user to attempt the other user's workout on the treadmill.

Portable computing device 101 or equipment computing devices 102*a*-102*n* can also be used to display educational information or sales opportunities. For example, a device may output information regarding the value of increasing the quality of the calories that are consumed to allow the user to lose weight while still having energy to perform the exercises. Similarly, a device may output a sales offer for new shoes or exercise clothing. Likewise, a device can output a notice of a competition which others have started or celebrity workouts that are available for the user to attempt to emulate.

FIG. 200 illustrates a flowchart of an exemplary method 200 for providing a dynamically updated diet and exercise plan. Method 200 can be performed by a mobile phone, a scale, or another computing device configured to communicate with exercise computing devices.

Method 200 includes an act 201 of receiving, by a computing device, a diet and exercise plan of a user, the diet and exercise plan including a target number of calories to burn during a time period, the target number of calories being based on the number of calories consumed by the user in the time period and a total number of calories burned by the user during the time period. For example, a diet and exercise plan can be received by a user's mobile phone (e.g. over the internet, from a scale or another computing device, etc.). Similarly, a plan can be received by a scale (e.g. over the internet, from a user's portable computing device, etc.).

Method 200 includes an act 202 of generating and displaying, to the user, a first recommended workout to perform using a first of a plurality of exercise devices. For example, a recommended treadmill workout can be presented to the user. The treadmill workout can be customized (e.g. in intensity or duration) based on the target number of calories to burn as defined in the user's plan, Method 200 includes an act 203 of receiving, from the first exercise device and in response to the user using the first exercise device, a number of calories burned by the user while using the first exercise device. For example, after the user has used the treadmill, the user's performance on the treadmill can be sent to the computing device for use in determining whether to dynamically update the user's plan.

Method 200 includes an act 204 of deducting the number of calories burned by the user while using the first exercise device from the target number of calories. For example, a remaining number of calories to burn during the applicable time period (e.g. a day) can be determined.

Method 200 includes an act 205 of, based on the target number of calories that remain after the deduction of the number of calories burned by the user while using the first exercise device, generating and displaying to the user, a second recommended workout to perform using a second of the plurality of exercise devices. For example, based on the remaining number of calories to be burned by the user during the time period, the next workout recommended can be a modified version of a workout in the plan (e.g. by increasing or decreasing the calories intended to be burned during the modified version of the workout), or a new recommended workout added to the plan (e.g. a workout that targets a different muscle group).

Accordingly, the present invention facilitates the tracking of a user's compliance with a diet and exercise plan, and allows the dynamic updating of a plan to ensure the user is guided more effectively to comply with the plan. The present invention also allows this tracking and modification to be performed at a central location such as on the user's smart phone, on a scale in a gym, or on another computing device. In this way, the plan can be adapted in real time to provide the most effective recommendations and motivation to the user while the user works out.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. A method, performed by a computing device, for dynamically updating a diet and exercise plan based on one or more exercises performed on one or more exercise devices, the method comprising;
   receiving, by a computing device, a diet and exercise plan of a user, the diet and exercise plan including a target number of calories to burn during a time period, the target number of calories being based on the number of calories consumed by the user in the time period and a total number of calories burned by the user during the time period;
   generating and displaying, to the user, a first recommended workout to perform using a first of a plurality of exercise devices;
   receiving, from the first exercise device and in response to the user using the first exercise device, a number of calories burned by the user while using the first exercise device;
   deducting the number of calories burned by the user while using the first exercise device from the target number of calories;
   based on the target number of calories that remain after the deduction of the number of calories burned by the user while using the first exercise device, generating and displaying to the user, a second recommended workout to perform using a second of the plurality of exercise devices;
   receiving, from a third exercise device and in response to the user using the third exercise device, a number of calories burned by the user while using the third exercise device;
   determining that the user used the third exercise device rather than performing the second recommended workout on the second exercise device; and
   modifying the diet and exercise plan by recommending a third recommended workout to perform using one of the plurality of exercise devices, the third recommended workout being generated based on the type of workout that was performed on the third exercise device so as to not recommend a workout that uses the same muscle group that was used on the third exercise device.

2. The method of claim 1, wherein the computing device is a portable computing device carried by the user.

3. The method of claim 2, wherein the portable computing device is a mobile phone.

4. The method of claim 1, wherein the computing device is incorporated into a scale.

5. The method of claim 4, wherein the computing device incorporated into the scale receives the number of calories burned by the user while using the first exercise device via a portable computing device carried by the user.

6. The method of claim 1, wherein the time period comprises a day.

7. The method of claim 1, wherein the number of calories consumed by the user is based at least partially on estimates generated using photographs of food consumed by the user during the time period.

8. The method of claim 1, wherein the first recommended workout includes a recommended number of calories to burn while using the first exercise device, and wherein the received number of calories burned by the user while using the first exercise device is less than the recommended number, the method further comprising:
   modifying the diet and exercise plan by modifying another recommended workout in the plan to increase the amount or intensity of the other recommend workout.

9. The method of claim 1, wherein the first recommended workout includes a recommended number of calories to burn while using the first exercise device, and wherein the received number of calories burned by the user while using the first exercise device is less than the recommended number, the method further comprising:
   modifying the diet and exercise plan by adding another recommended workout to the plan.

10. The method of claim 1, wherein the first recommended workout includes a recommended number of calories to burn while using the first exercise device, and wherein the received number of calories burned by the user while using the first exercise device is greater than the recommended number, the method further comprising:
    modifying the diet and exercise plan by modifying another recommended workout in the plan to decrease the amount or intensity of the other recommend workout.

11. The method of claim 1, wherein the first recommended workout includes a recommended number of calories to burn while using the first exercise device, and wherein the received number of calories burned by the user while using the first exercise device is greater than the recommended number, the method further comprising:
    modifying the diet and exercise plan by removing another recommended workout to the plan.

12. The method of claim 1, further comprising:
  determining that the user has burned more calories during the time period than the target number of calories; and
  modifying the diet and exercise plan to recommend that the user consume more calories.

13. The method of claim 1, further comprising:
  determining that the user has consumed more calories during the time period than the target number of calories; and
  modifying the diet and exercise plan one or more of:
    modifying a recommended workout in the plan by increasing the amount or intensity of the recommended workout; or
    adding a recommended workout to the plan.

14. The method of claim 1, wherein at least one recommended workout in the diet and exercise plan comprises one or more of:
  a workout performed by another user;
  a workout recommended by another user; or
  a workout contained in another user's diet and exercise plan.

15. The method of claim 1, further comprising:
  transmitting the user's diet and exercise plan to a server for display within a social media environment.

16. A computing device comprising:
  one or more processors; and
  one or more computer storage media storing computer executable instructions which when executed by a processor perform a method for dynamically updating a diet and exercise plan based on one or more exercises performed on one or more exercise devices, the method comprising:
    receiving a diet and exercise plan of a user, the diet and exercise plan including a target number of calories to burn during a time period, the target number of calories being based on the number of calories consumed by the user in the time period and a total number of calories burned by the user during the time period;
    generating and displaying, to the user, a first recommended workout to perform using a first of a plurality of exercise devices;
    receiving, from the first exercise device and in response to the user using the first exercise device, a number of calories burned by the user while using the first exercise device;
    deducting the number of calories burned by the user while using the first exercise device from the target number of calories;
    based on the target number of calories that remain after the deduction of the number of calories burned by the user while using the first exercise device, generating and displaying to the user, a second recommended workout to perform using a second of the plurality of exercise devices;
    receiving, from a third exercise device and in response to the user using the third exercise device, a number of calories burned by the user while using the third exercise device;
    determining that the user used the third exercise device rather than performing the second recommended workout on the second exercise device; and
    modifying the diet and exercise plan by recommending a third recommended workout to perform using one of the plurality of exercise devices, the third recommended workout being generated based on the type of workout that was performed on the third exercise device so as to not recommend a workout that uses the same muscle group that was used on the third exercise device.

17. The computing device of claim 16, wherein the computing device comprises:
  a mobile phone carried by the user; or
  a scale configured to communicate with one or more of:
    a mobile phone carried by the user; or
    one or more of the plurality of exercise devices.

18. The computing device of claim 17, wherein the mobile phone or scale is configured to:
  receive a diet and exercise plan or a portion of a diet and exercise plan of another user and modify the user's diet and exercise plan based on the diet and exercise plan or portion of the diet and exercise plan of the other user; or
  transmit the user's diet and exercise plan or a portion of the user's diet and exercise plan to a server for display in a social media environment.

19. The computing device of claim 18 wherein the received diet and exercise plan or portion of a diet and exercise plan of the other user comprises one or more workouts completed or recommended by the other user; and
  wherein the transmitted diet and exercise plan or portion of a diet and exercise plan of the user comprises one or more workouts completed or recommended by the user.

* * * * *